United States Patent
Lin et al.

(10) Patent No.: US 6,177,672 B1
(45) Date of Patent: Jan. 23, 2001

(54) DUAL-CHAMBER GAS SAMPLING DEVICE

(75) Inventors: Yao Min Lin; Yung Hsin Chen, both of Hsinchu; Jack Chen, Taipei, all of (TW)

(73) Assignee: Industrial Technology Research Institute, Hsinchu (TW)

( * ) Notice: Under 35 U.S.C. 154(b), the term of this patent shall be extended for 0 days.

(21) Appl. No.: 09/220,474

(22) Filed: Dec. 23, 1998

(30) Foreign Application Priority Data

Jun. 29, 1998 (CN) ................................................ 87210414

(51) Int. Cl.⁷ ............................. G01N 1/22; G01N 1/44; G01N 21/61
(52) U.S. Cl. .................................... 250/338.5; 73/863.11; 73/863.23; 250/343; 356/36
(58) Field of Search ............................. 250/338.5, 343; 356/36; 73/863.23, 863.11, 863.12

(56) References Cited

U.S. PATENT DOCUMENTS

| | | | |
|---|---|---|---|
| 4,363,635 | * 12/1982 | Hutson | 250/343 X |
| 4,709,159 | 11/1987 | Pace | 307/227 |
| 4,799,374 | * 1/1989 | Bossert et al. | 73/863.23 X |
| 5,162,233 | * 11/1992 | Kamori et al. | 73/863.11 X |
| 5,163,332 | 11/1992 | Wong | 73/863.23 |
| 5,453,620 | 9/1995 | Wadsworth et al. | 250/343 |

FOREIGN PATENT DOCUMENTS

| | | | |
|---|---|---|---|
| 6-94586 | * 4/1994 | (JP) | 73/23.2 |
| 9-33406 | * 2/1997 | (JP) | |
| 9-229831 | * 9/1997 | (JP) | |

* cited by examiner

*Primary Examiner*—Thomas P. Noland
(74) *Attorney, Agent, or Firm*—Kenyon & Kenyon

(57) ABSTRACT

The present invention relates to an improved gas sampling device comprising a pair of hollow rectangular chambers having diffusion apertures, a heat insulating plate, a reflecting element, a light source and a light detector; wherein the pair of rectangular chambers are arranged one over the other, with the heat insulating element being placed therebetween, the reflecting element having two reflecting surfaces at right angle with respect to each other, one end of the rectangular chambers being secured to the reflecting element with each end thereof being aligned with a reflecting surface, the light source and the light detector being placed at the other end respectively of the rectangular chambers. In use, the rectangular chambers are placed horizontally with the light source being in the lower chamber such that when light is emitted from the light source, light rays pass through the lower chamber and are reflected by the reflecting surface to enter into the upper chamber and, finally, received by the light detector. The concentration of the gas can be measured by analyzing the variation in intensity resulted from the specific wavelength of the infrared light absorbed in the chambers by the gas to be measured. With the light source being packed in a metal, gas sampling rate is increased with the gas flowing into the upper chamber by the convection due to the higher temperature in the lower chamber than that in the upper chamber when light is emitted.

2 Claims, 1 Drawing Sheet

DUAL-CHAMBER GAS SAMPLING DEVICE

BACKGROUND OF THE INVENTION

1. Field of the Invention

The present invention relates to a gas sampling device and, in particular, to a dual-chamber gas sampling device using thermal convection for accelerating gas diffusion rate, which can be used in all non-dispersive infrared (NDIR) gas concentration analyzer, and for improving the sampling rate and reducing the length of the device.

2. Description of Related Art

A gas sampling device is required for conventional non-dispersive infrared (NDIR) gas concentration analyzer. With prior art gas sampling devices, a gas pump or fan is used such that gas is introduced into a gas chamber by forced convection. By doing so, while reaction time is reduced, a lot of problems, such as noise, vibration, interference due to the noise, excessive power consumption, etc., are caused, thus rendering them unsuitable for use in hand-held or pocket-size battery operated apparatuses. Therefore, there have been gas sampling devices in which chamber of porous materials or chamber having diffusion apertures left all around are utilized. Gas sampling is achieved by using the difference in concentration to generate diffusion. These devices, however, have disadvantages in that the reaction time is relative longer and the chamber has to be longer in length for sufficient sensitivity.

In view of the disadvantages encountered by conventional gas sampling devices described above, the present invention provides a dual-chamber gas sampling device in which, in addition to the diffusion apertures provided on the gas chamber, the temperature difference between the upper and lower chambers is used to increase the gas diffusion rate such that the reaction time is reduced. At the same time, the reflecting surfaces of the reflecting elements which are at right angle with respect to each other are used for transmitting light rays so as to serve the purpose for analyzing gas concentration by non-dispersive infrared, and a single chamber can thus be divided into two chambers for improved arrangement such that the size of the device can be further reduced.

SUMMARY OF THE INVENTION

The present invention provides a dual-chamber gas sampling device characterized in that the length of the device is reduced by allowing light to pass through a chamber, be reflected, and then pass through another chamber, and in that the gas sampling rate is improved by means of diffusion by concentration and diffusion by thermal, without requiring additional power for driving. The light source, light detector and the chambers are all basic elements found in the non-dispersive infrared gas concentration analyzers.

An object of the present invention is to provide an improved dual-chamber gas sampling device which has improved sampling rate and reduced length of the device for convenient arrangement and thus is compact in size.

Figure 1:
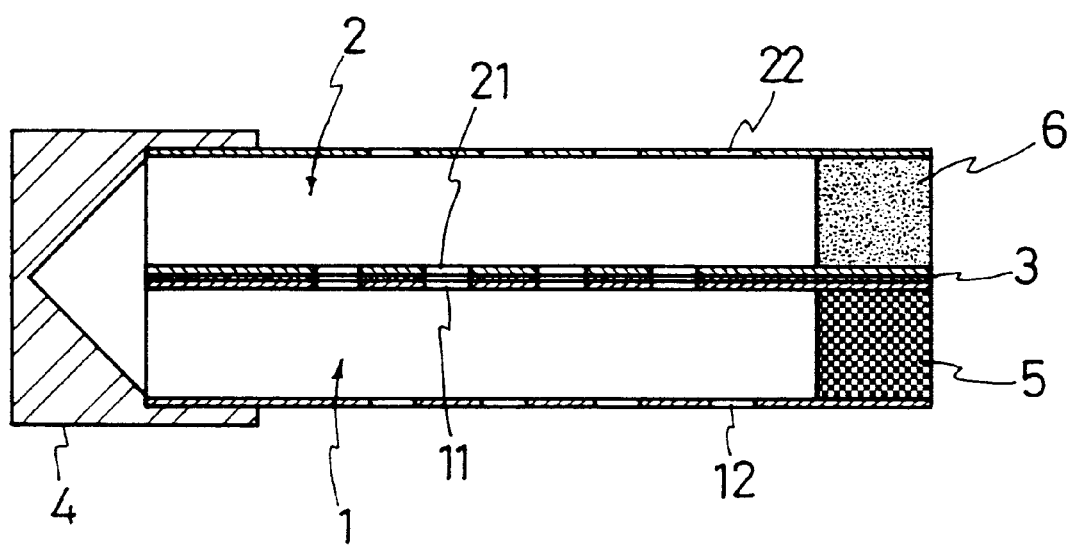
FIG. 1 shows a dual-chamber gas sampling device of the present invention.

LIST OF REFERENCE NUMERALS 1 lower sampling chamber
2 upper sampling chamber
3 heat insulating plate
4 reflecting element
5 light source
6 light detector
11 diffusion apertures
12 outside diffusion apertures and gas filters
21 diffusion apertures
22 outside diffusion apertures and gas filters

DETAILED DESCRIPTION OF THE INVENTION

The principle for a non-dispersive infrared gas analyzer is based on the Beer's Law: A=abc, where A is absorption of the gas, a is absorption coefficient, b is the length of the optical path, and c is the concentration of the gas. Therefore, the sensitivity of the analyzer is in direct proportion to the length of the optical path. As a result, it can be known that the sampling chamber must be sufficiently long to achieve a certain desired sensitivity. This is the reason why conventional sampling chamber is rather long in length.

The gas in the gas sampling device is caused to diffuse by concentration difference or by forced convection by using a fan or a pump, or by thermal convection. In conventional sampling chamber equipped with a fan or a pump, while the sampling rate is increased, there are the disadvantages of noise, vibration, interference due to the noise, excessive power consumption, etc., thus rendering them unsuitable for use with battery operated hand-held or pocket- size analyzers. On the other hand. Sampling device with a single diffusion chamber have the disadvantage of low sampling rate because only diffusion of concentration difference is used In the dual-chamber sampling device of the present invention, the optical path is distributed in the upper and lower sampling chambers such that the overall length of the device is reduced, and in addition to the diffusion apertures, the gas sampling rate is increased by thermal convection generated by the temperature difference between the upper and lower chambers. Both concentration difference and thermal convection for creating gas diffusion are incorporated in the design of the present invention.

Since both concentration difference and thermal convection for creating gas diffusion are utilized, the dual-chamber sampling device of the present invention can be used to achieve an optimized result by having the device placed horizontally (as shown in FIG. 1). The dual-chamber sampling device includes an upper and a lower sampling chambers 2, 1, a heat insulating plate 3, a reflecting element 4, a light source 5, and a light detector 6. The light source 5 is mounted at one end of the lower sampling chamber 1, and the light detector 6 is mounted at one end of the upper sampling chamber 2. The other ends of both the upper and lower sampling chambers are secured to the reflecting element 4. The inner surface of both the upper and lower sampling chambers are hollow rectangular tubular elements having a smooth surface for increasing reflection of light rays. The reflecting element 4 has two reflecting surfaces at right angle with respect to each other for reflecting light rays from the lower chamber to the upper chamber and for securing the upper and lower chambers. The housing of the light source 5 is made of a heat conductive material such that when the device is actuated, the heat generated from the housing will heat the lower sampling chamber 1, and the heat insulating plate 3 between the lower sampling chamber 1 and the upper sampling chamber 2 will prevent heat from transmitting into the upper sampling chamber 2 from the lower sampling chamber 1 such that the lower sampling chamber 1 will be at a temperature higher than the upper sampling chamber 2. As a result, thermal convection is generated, causing the gas to diffuse up quickly into the lower sampling chamber 1, and then into the upper sampling chamber 2. In addition, both the lower and upper sampling chamber 1, 2 have diffusion apertures 11, 21, allowing the gas to diffuse into the sampling chambers 1, 2 for increasing the gas sampling rate. The diffusion apertures on the outside of the upper and lower sampling chambers are equipped with air filters 12, 22 for blocking off dust.

The dual-chamber sampling device of the present invention has its optical path as described below. The light rays emitted from the light source 5 are converged into parallel light beams and enter the lower sampling chamber 1 to react with the gas. The lower sampling chamber 1 with its inner surface having a smooth surface (which can be treated by polishing or film-plating) can increase light reflection. The light beams from the lower sampling chamber 1 are reflected by the reflecting surfaces of the reflecting element 4 having surfaces which are at right angle with respect to each other then enter the upper sampling chamber 2 and remain as parallel light beams and react with the gas. The upper sampling chamber 2 also has a smooth inner surface. Finally, light beams reach the light detector 6, and gas concentration can be measured by analyzing its variation and other subsequent treatments.

While the present invention has been described by way of the embodiment thereof, the scope of the present invention is not limited thereto. Alterations and modifications can be made by those skilled in the art without departing from the spirit and scope of the present invention. Therefore, it is intended that the present invention is limited only by the scope as defined in the appended claims.

What is claimed is:

1. A dual-chamber sampling device, comprising an upper sampling chamber, a lower sampling chamber located under said upper sampling chamber, a heat insulating plate disposed between said upper and lower sampling chambers, a reflecting element disposed on one end of said upper and lower sampling chambers for securing said upper and lower sampling chambers, and a light source and a light detector mounted respectively on the other end of said upper and lower sampling chambers, wherein said upper and lower sampling chambers have diffusion apertures for enhancing gas diffusion and said reflecting element has two reflecting surfaces which are at right angle with respect to each other for distributing the optical path in said upper and lower sampling chambers such that the device is reduced in length.

2. The dual-chamber sampling device according to claim 1, wherein thermal convection is created by the temperature difference of the upper and lower sampling chambers due to the heat generated by said light source, thereby to enhance gas diffusion and to increase the gas sampling rate.

* * * * *